(12) United States Patent
Daikai et al.

(10) Patent No.: US 6,201,123 B1
(45) Date of Patent: Mar. 13, 2001

(54) CATALYST COMPOSITION, CATALYST SOLUTION AND PROCESS FOR PREPARING OPTICALLY ACTIVE EPOXIDE

(75) Inventors: Kazuhiro Daikai, Fukuoka; Masahiro Kamaura, Kagoshima; Takeshi Hanamoto; Junji Inanaga, both of Fukuoka, all of (JP)

(73) Assignee: Techno Polymer Co., Ltd., Tokyo (JP)

( * ) Notice: Subject to any disclaimer, the term of this patent is extended or adjusted under 35 U.S.C. 154(b) by 0 days.

(21) Appl. No.: 09/315,728

(22) Filed: May 21, 1999

(30) Foreign Application Priority Data

Jul. 8, 1998 (JP) .................................................. 10-192743

(51) Int. Cl.$^7$ ..................... C07C 39/205; C07D 233/54; C07F 9/54
(52) U.S. Cl. ............................. 546/21; 548/341.1; 568/9; 568/367; 568/382; 568/717; 502/302; 502/303; 502/304
(58) Field of Search ..................................... 502/302, 303, 502/304; 546/21; 548/341.1; 568/9, 367, 382, 717

(56) References Cited

FOREIGN PATENT DOCUMENTS 10-120668    5/1998 (JP) .

OTHER PUBLICATIONS

Daikai et al: "Remarkable Ligand Effect on the Enantioselectivity of the Chiral Lanthanum Complex–Catalyzed Asymmetric Epoxidation of Enones," pp.7321–7322, 1998.

J. Am. Chem. Soc., vol. 119, No. 9, 1997, p. 2329–2330, etc.

Primary Examiner—Joseph K. McKane
Assistant Examiner—Taofiq A. Solola
(74) Attorney, Agent, or Firm—Nixon & Vanderhye

(57) ABSTRACT

A catalyst composition for organic a symmetric synthesis is provided, which comprises:

(A) a lanthanoid element ion;
(B) a binaphthol, and
(C) a nitrogen and/or phosphorus compound such as lutidine-N-oxide, 1,3-dimethyl-2-imidazolldinone, hexamethyl-phosphortriamide, triphenylphosphine oxide, tri(2-methylphenyl)phosphine oxide or tri(4-methylphenyl )phosphine oxide. Asymmetric epoxidation of an enone is conducted by allowing an enone to react with an oxidizing agent in the presence of the catalyst composition or a catalyst solution containing the catalyst composition.

8 Claims, No Drawings

CATALYST COMPOSITION, CATALYST SOLUTION AND PROCESS FOR PREPARING OPTICALLY ACTIVE EPOXIDE

BACKGROUND OF THE INVENTION (1) Field of the Invention

This invention relates to a catalyst composition for organic asymmetric synthesis, a catalyst solution comprising the catalyst composition, and a process for preparing an optically active epoxide by catalytic asymmetric epoxidation.

The catalyst composition of the present invention is useful for various organic asymmetric syntheses. For example, it exhibits a high catalytic activity for asymmetric epoxidation of enones and gives epoxides having an enhanced optical purity.

(2) Description of the Related Art

As for catalysts for organic asymmetric syntheses, a catalyst solution has been heretofore proposed for asymmetric epoxidation in Japanese Unexamined Patent Publication No. H10-120668, which comprises (A) lanthanum isopropoxide, (B) a binaphthol derivative represented by the following general formula (6):

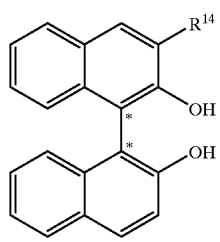

(6)

wherein $R^{14}$ is hydrogen or a hydroxymethyl group, and * signifies that the carbon atom adjacent thereto is optically active, (C) a molecular sieve 4A, and (D) tetrahydrofuran.

However, when the catalytic asymmetric epoxidation is conducted by using tert-butylhydroperoxide (hereinafter abbreviated to "TBHP") as an oxidizing agent and, for example, at room temperature for 30 minutes, an epoxide with a low optical purity of 73% is obtained in a low yield of 86%. If the catalytic asymmetric epoxidation is conducted by using a special oxidizing agent, i.e., cumene hydroperoxide (hereinafter abbreviated to "CMHP") and, for example, for at least 6 hours, then, epoxides with an optical purity of 83 to 94% are obtained in a yield of 78 to 98% (J. Am. Chem. Soc. Vol. 119, No. 9, 1997, p2329–2330).

SUMMARY OF THE INVENTION

A primary object of the present invention is to provide a catalyst composition exhibiting an enhanced catalytic activity for organic asymmetric synthesis and giving a reaction product with a high optical purity.

In accordance with the present invention, there is provided a catalyst composition for organic asymmetric synthesis comprising:

(A) a lanthanoid element ion;

(B) a binaphthol represented by the following general formula (1):

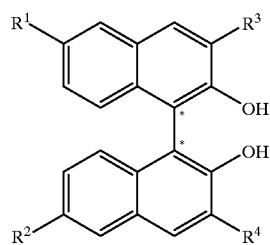

(1)

wherein $R^1$, $R^2$, $R^3$ and $R^4$ independently represent a hydrogen atom, a straight chain, branched chain or cyclic alkyl group having 1 to 10 carbon atoms, a straight chain, branched chain or cyclic alkoxy group having 1 to 10 carbon atoms, a straight chain, branched chain or cyclic alkyloxyalkyl group having 2 to 10 carbon atoms, a straight chain, branched chain or cyclic alkyloxyalkoxy group having 2 to 10 carbon atoms, a straight chain, branched chain or cyclic alkylamino group having 1 to 10 carbon atoms, an aromatic group having 5 to 14 carbon atoms, an aromatic group having 5 to 14 carbon atoms and having a substituent which is an alkyl group having 1 to 5 carbon atoms, or a halogen atom; and * signifies that the carbon atom adjacent thereto is optically active; and (C) at least one compound selected from the group consisting of:

(i) compounds represented by the following general formula (2):

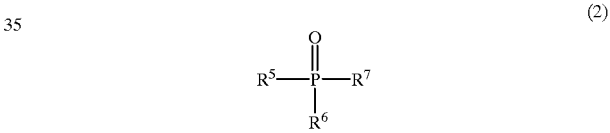

(2)

wherein $R^5$, $R^6$ and $R^7$ independently represent a straight chain, branched chain or cyclic alkyl group having 1 to 10 carbon atoms, an aromatic group having 5 to 14 carbon atoms, an aromatic group having 5 to 14 carbon atoms and having a substituent which is an alkyl group with 1 to 5 carbon atoms, or a group represented by the following formula:

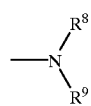

wherein $R^8$ and $R^9$ independently represent a straight chain, branched chain or cyclic alkyl group having 1 to 10 carbon atoms, an aromatic group having 5 to 14 carbon atoms, a straight chain, branched chain or cyclic alkyl group having 1 to 5 carbon atoms and having a substituent which is an aromatic group with 5 to 14 carbon atoms, or an aromatic group having a substituent which is an aromatic group with 5 to 14 carbon atoms, and $R^8$ and $R^9$ may be combined together to form an alkylene group having 2 to 6 carbon atoms; and (ii) compounds represented by the following general formula (3):

(3)

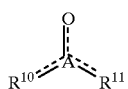

wherein A represents a carbon or nitrogen atom; and, when A is a carbon atom, $R^{10}$ and $R^{11}$ independently represent an amino group having two substituents each of which is a straight chain, branched chain or cyclic alkyl group having 1 to 10 carbon atoms, wherein $R^{10}$ and $R^{11}$ may be combined together with A to form a nitrogen-containing ring, or $R^{10}$ and $R^{11}$ independently represent an amino group having two substituents each of which is an aromatic group having 5 to 14 carbon atoms, and the bond between A and O is a double bond; and, when A is a nitrogen atom, $R^{10\ and\ R11}$ are combined together with A to form a nitrogen-containing aromatic ring, and the bond between A and O is a single bond.

In accordance with the present invention, there is further provided a catalyst solution for organic asymmetric synthesis comprising the above-mentioned catalyst composition and an ether solvent.

In accordance with the present invention, there is further provided a process for preparing an optically active epoxide represented by the following general formula (5):

(5)

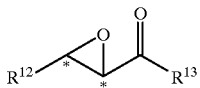

wherein $R^{12}$ and $R^{13}$ independently represent a straight chain, branched chain or cyclic alkyl group having 1 to 20 carbon atoms, an aromatic group having 5 to 14 carbon atoms, an aromatic group having 5 to 14 carbon atoms and having one to five substituents which are an alkyl group having 1 to 5 carbon atoms, an aromatic group having 5 to 14 carbon atoms and having one to five substituents which are an alkoxy group having 1 to 5 carbon atoms, an aromatic group having 5 to 14 carbon atoms and having one to five substituents which are a halogen atom, a straight chain, branched chain or cyclic alkly group having 1 to 6 carbon atoms and having a substituent which is an aromatic group having 5 to 14 carbon atoms, or a straight chain, branched chain or cyclic alkyl group having 1 to 5 carbon atoms and having a substituent which is a halogenated aromatic group having 5 to 14 carbon atoms, and * signifies that the carbon atom adjacent thereto is optically active, which comprises comprising allowing an enone represented by the following general formula (4) to react with an oxidizing agent in the presence of the above-mentioned catalyst composition or the above-mentioned catalyst solution, (4)

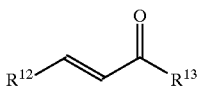

wherein $R^{12}$ and $R^{13}$ are as defined above for the formula (5).

DETAILED DESCRIPTION OF THE PREFERRED EMBODIMENTS

The catalyst composition of the present invention comprises (A) a lanthanoid element ion, (B) a binaphthol of the above formula (1), and (C) at least one compound selected from compounds of the above general formula (2) and compounds of the above general formula (3). The catalyst composition broadly includes various types of compositions, which include compositions, the ingredients of which are bound together not only through an ionic bonding-coordinate bond, but also through a covalent bonding-coordinate bond. To make the following explanation short and clear, the respective ingredients will be explained on an ionic form.

The lanthanoid element ion (A) used is not particularly limited, and usually includes ions of elements selected from scandium, yttrium, lanthanum, cerium, praseodymium, neodymium, samarium, europium, gadolinium, terbium, dysprosium, holmium, erbium, thulium, ytterbium and lutecium.

The lanthanoid element ions can be obtained from, for example, their alkoxides prepared from the corresponding aliphatic alcohols, such as methoxide, ethoxide, n-propoxide, isopropoxide and n-propoxide; their sulfonates such as trifluoromethane sulfonate and pentafluoroethane sulfonate; and their halides such as chloride, bromide and iodide.

The binaphthol of the formula (1), i.e., ingredient (B) in the catalyst composition of the invention, is not particularly limited. As specific examples of the binaphthol, there can be mentioned (R) compounds such as (R)-binaphthol, (R)-3,3'-dimethoxyblnaphthol, (R)-3,3'-methoxyethoxybinaphthol, (R)-6,6'-diphenylbnaphthol, (R)-6,6'-dibromobinaphthol, (R)-6,6'-dinaphthylbinaphthol and (R)-6,6'-dimethoxybinaphthol; and (S) compounds which are enantomers of the (R) compounds, such as (S)-binaphthol, (S)-3,3'-dimethoxybinaphthol, (S)-3,3'-methoxyethoxybinaphthol, (S)-6,6'-diphenylbinaphthol, (S)-6,6'-dibromobinaphthol, (S)-6,6'-dinaphthylbinaphthol and (S)-6,6'-dimethoxybinaphthol. These binaphthols can be appropriately chosen depending upon the particular object of the catalyst composition.

The ingredient (C) in the catalyst composition of the invention is not particularly limited provided that it is at least one compound selected from compounds of the formula (2) and compounds of the formula (3).

As specific examples of the compounds of the formula (2), there can be mentioned phosphine oxides such as triphenylphosphine oxide, tri(2-methylphenyl)phosphine oxide, tri(3-methylphenyl)-phosphine oxide, tri(4-methylphenyl)phosphine oxide, methyldiphenylphosphine oxide, methoxymethyldiphenylphosphine oxide, tri-n-butylphosphine oxide, tri-n-octylphosphine oxide and tri (cyclohexyl)phosphine oxide; and phosphortriamides such as hexamethylphosphortriamide and tripiperidinophosphine oxide. As specific examples of the compounds of the formula (3), there can be mentioned 1,3-dimethyl-2-imidazolidinone and 2,6-lutidine-N-oxide. Of these compounds of the formulae (2) and (3), the compounds of the formula (2) are preferable. Ttriphenylphosphine oxide, tri (p-methylphenyl)phosphine oxide, hexamethylphosphortriamide and tripiperidinophosphine oxide are especially preferable.

In the catalyst composition of the invention, an anion or cation is preferably incorporated therein to counterbalance the electrical charge. More specifically, the lanthanoid element ion (A) has a valency of 3, and therefore, when the amount of the binaphthol (B) is at least 1.5 moles per mole of (A), a cation is incorporated, and, when the amount of the binaphthol is smaller than 1.5 moles per mole of (A), an anion is used.

The cation used is not particularly limited and usually includes alkali metal ions and alkaline earth metal ions. As specific examples of the cation, there can be mentioned lithium ion, sodium Ion, potassium ion, rubidium ion, beryllium ion, magnesium ion, calcium ion, strontium ion and barium ion.

The anion also is not particularly limited, and includes, for example, straight chain, branched chain or cyclic alkyloxy ions having 1 to 20 carbon atoms; straight chain, branched chain or cyclic alkylthio ions having 1 to 20 carbon atoms; alkyloxy ions having 1 to 8 carbon atoms and having an aromatic substituent having 5 to 12 carbon atoms: alkylthio ions having 1 to 8 carbon atoms and having an aromatic substituent having 5 to 12 carbon atoms; halogen ions; perhalogen acid ions; tetrafluoroborane ions; and fluorinated alkylsulfonic acid ions. As specific examples of the anion, there can be mentioned methoxy ion, ethoxy ion, n-propoxy ion, isopropoxy ion, n-butoxy ion, isobutoxy ion, tert-butoxy ion, n-pentoxy ion, isopentoxy ion, cyclopentoxy ion, n-hexyloxy ion, isohexyloxy ion, cyclohexyloxy ion, n-heptyloxy ion, n-octyloxy ion, 2-cyclohexylethoxy ion, n-nonyloxy ion, n-undecyloxy ion, n-pentadecyloxy ion, methylthio ion, ethylthio ion, n-propylthio ion, isopropylthio ion, n-butylthio ion, isobutylthio ion, tert-butylthio ion, n-pentylthio ion, isopentylthio ion, cyclopentylthio ion, n-hexylthio ion, isohexylthio ion, cyclohexylthio ion, n-heptylthio ion, n-octylthio ion, 2-cyclohexylethylthio ion, n-nonylthio ion, n-undecylthio ion, n-pentadecylthio ion, benzyloxy ion, diphenylmethyloxy ion, benzylthio ion, diphenylmethylthio ion, fluorine ion, chlorine ion, bromine ion, iodine ion, perchlorate ion, perbromate ion, periodate ion, tetrafluoroborate ion, trifluoromethanesulfonate ion and pentafluoroethanesulfonate ion. Of these anions, alkyloxide ions and aralkyloxide ions are preferable. More specifically, methoxy ion, ethoxy ion, n-propoxy ion, isopropoxy ion, n-butoxy ion, isobutoxy ion, tert-butoxy ion, chlorine ion, bromine ion, iodine ion, perchlorate ion, perbromate ion, periodate ion, tetrafluoroborate ion, trifluoromethanesulfonate ion and pentafluoroethanesulfonate ion.

The proportion of the three ingredients (A), (B) and (C) in the catalyst composition of the invention is not particularly limited, but usually, the catalyst composition comprises (A) 1 mole of the lanthanoid element ion; (B) 1 to 3 moles of the binaphthol of the general formula (1); and (C) 1 to 10 moles of at least one compound selected from the group consisting of (i) compounds of the formula (2) and (ii) compounds of the formula (3).

The procedure by which the catalyst composition of the invention is prepared is not particularly limited. For example, the catalyst composition is prepared by allowing the lanthanoid element ion (A), the binaphthol (B) of the formula (1), and at least one compound (C) selected from compounds of the formula (2) and compounds of the formula (3) to react with each other in a solvent.

The solvent used for the preparation of the catalyst composition is not particularly limited provided that it is inert to the catalyst composition and to the reaction involved. However, in view of stability of the catalyst and results of the organic asymmetric synthesis, ether solvents such as dimethyl ether, diisopropyl ether, 1,2-dimethoxyethane and tetrahydrofuran (hereinafter abbreviated to "THF") are preferable.

The thus-prepared catalyst composition can be used for the organic asymmetric synthesis as it is.

The catalyst composition of the invention exhibits a high catalytic activity in various organic asymmetric syntheses and gives reaction products with a high optical purity, although the suitable reaction varies depending upon the kind of the lanthanoid element ion and the proportion of the catalyst ingredients. The organic asymmetric synthesis reactions include various asymmetry-inducing reactions, for example, asymmetric aldol condensation reaction, asymmetric epoxidation reaction, asymmetric Diels-Alder cyclization reaction, asymmetric hetero-Diels-Alder cyclization reaction, asymmetric reduction reaction, asymmetric protonation reaction, asymmetric nitro-aldol reaction, asymmetric Michael addition reaction, asymmetric hydrophosphonylation reaction and asymmetric Michael-aldol reaction.

The optical absolute configuration manifested by the asymmetric synthesis using the catalyst composition of the invention generally depends upon the particular optical absolute configuration of the binaphthol (B) contained in the catalyst composition. For example, assuming that, when a substrate is subjected to the asymmetric synthesis using the catalyst composition comprising an (R)-binaphthol, the asymmetric carbon of the reaction product is of an (R)-optical absolute configuration. Then, when the same substrate is subjected to the asymmetric synthesis using the catalyst composition comprising (S)-binaphthol, the asymmetric carbon of the reaction product is of an (S)-optical absolute configuration. It is to be noted that, when a substrate is subjected to the asymmetric synthesis using the catalyst comprising an (R)-naphthol, the asymmetric carbon of the reaction product is not always of an (R)-optical absolute configuration. The optical absolute configuration of the reaction product varies depending upon the particular substrate used and the other factors.

The amount of the catalyst composition of the invention used for the organic asymmetric synthesis is not particularly limited, but is usually in the range of 0.01 to 50% by mole, preferably 0.1 to 25% by mole, based on the lanthanoid element ion.

The organic asymmetric synthesis using the catalyst composition of the invention will now be specifically described as for an asymmetric epoxidation reaction of an enone which is a typical example for which the catalyst composition is applied. But, the invention should not be construed to be limited by the asymmetric epoxidation reaction.

When the catalyst composition of the invention is used for the asymmetric epoxidation of an enone, it is preferably used in the form of a previously prepared solution of the catalyst composition. The solution of the catalyst is preferably prepared by allowing the lanthanoid element ion (A), the binaphthol element (B) of the formula (1), and at least one compound (C) selected from compounds of the formula (2) and compounds of the formula (3) to react with each other in an ether solvent. The ether solvent includes, for example, dimethyl ether, diisopropyl ether, 1,2-dimethoxyethane and THF.

The lanthanoid element ion (A) contained in the catalyst solution used for the asymmetric epoxidation of an enone is not particularly limited, but is preferably lanthanum ion. The lanthanum ion can be obtained from lanthanum alkoxides prepared from the corresponding aliphatic alcohols, such as lanthanum methoxide, lanthanum ethoxide, lanthanum n-propoxide, lanthanum isopropoxide and lanthanum n-butoxide; lanthanum sulfonates such as lanthanum trifluoromethanesulfonate and lanthanum pentafluoroethanesulfonate; and lanthanum halides such as lanthanum chloride, lanthanum bromide and lanthanum iodide.

As mentioned above, the amount of the binaphthol (B) of the formula (1) used is usually in the range of 1 to 3 moles per mole of the lanthanoid element ion (A). Theoretically, the use of equimolar amounts of the lanthanoid element ion (A) and the binaphthol (B) is optimum for the consideration of yield and optical purity of the epoxide produced. But, actually, the amount by mole of the lanthanoid element ion (A) should not exceed the amount by mole of the binaphthol (B), and especially preferably, the amount of the lanthanoid element ion (A) is in the range of 0.8 to 1.0 mole per mole of the binaphthol (B). In this case, the binaphthol (B) is present in an amount of smaller than 1.5 moles per mole of the lanthanoid element ion, and thus, about 1 mole of an anion of a lanthanoid element compound used for obtaining the lanthanoid element ion (A) is present for counterbalancing the electrical charge. The anion can be converted to another anion by subjecting it to a further reaction.

The compound (C) selected from compounds of the formula (2) and compounds of the formula (3) in the catalyst solution used for the asymmetric epoxidation of an enone, is not particularly limited. But, compounds of the formula (2) are preferable, and triphenylphosphine oxide, tri(4-methylphenyl)phosphine oxide, hexamethylphosphortriamide and tripiperidinophosphine oxide are more preferable.

The amount of the compound (C) selected from compounds of the formula (2) and compounds of the formula (3) in the catalyst solution is usually in the range of 1 to 10 moles per mole of the lanthanoid element ion (A), as mentioned above. The amount of the compound (C) is preferably at least 1.1 moles, more preferably at least 1.5 moles, per mole of the lanthanoid element ion (A) for the formation of a catalyst with enhanced stability.

The solvent used for the catalyst solution for the asymmetric epoxidation of an enone is not particularly limited provided that the solvent is inert to the catalyst and the epoxidation reaction. But, ethers such as dimethyl ether, diisopropyl ether, 1,-dimethoxyethane and THF are preferable, and THF is most preferable in view of stability of the catalyst and results of the epoxidation reaction, The amount of the solvent is usually in the range of 2 to 200 times by weight, preferably 5 to 100 times by weight, of the enone used.

The enone represented by the formula (4), used for the asymmetric epoxidation, is not particularly limited. As specific examples of the enone, there can be mentioned methyl vinyl ketone, trans-3-penten-2-one, trans-3-hexen-2-one, trans-3-hepten-2-one, trans-3-octen-2-one, trans-3-nonen-2-one, ethyl vinyl ketone, trans-4-hexen-3-one, trans-4-hepten-3-one, trans-4-octen-3-one, trans-4-nonen-3-one, isopropyl vinyl ketone, trans-2-methyl-4-hexen-3-one, trans-2-methyl-4-hepten-3-one, trans-2-methyl-4-octen-3-one, trans-2-methyl-4-nonen-3-one, trans-1,3-diphenyl-2-propen-1-one (i.e., chalcone), trans-2-methyl-5-phenyl-4-penten-3-one, 4-methyl-l-phenyl-3-penten-2-one, 4-phenyl-3-buten-2-one, 6-phenyl-3-hexen-2-one and 5-phenyl-3-hexen-2-one.

In the process of the present invention for asymmetric epoxidation of an enone, usually TBHP is used as an oxidizing agent. A commercially available solution of TBHP in decane or other solvents can be used as it is. Alternatively, TBHP is extracted with toluene from an aqueous solution with a 70% or 90% concentration, and dried with magnesium sulfate, and then used for the asymmetric epoxidation. Other oxidizing agents, for example, cumene peroxide can be used instead of TBHP. Theoretically, the amount of the oxidizing agent is may be equimolar to the enone used, but actually it is preferable to use at least 1.1 moles of the oxidizing agent per mole of the enone for completing the asymmetric epoxidation reaction within a reasonably short time.

The reaction temperature employed for the asymmetric epoxidation of an enone varies depending upon the particular enone used, but is usually in the range of −50° C. to 100° C. Usually the epoxidation reaction is completed within 24 hours, and, when triphenylphosphine oxide is used as the component (C), the reaction is generally completed within 2 hours.

Preferably a zeolite is used in an amount of approximately equal weight to the enone for the purpose of dehydrating the reaction mixture at the step of catalyst preparation or asymmetric epoxidation of the enone, or promoting the catalyst preparation reaction or the asymmetric epoxidation reaction. As specific examples of the zeolite, there can be mentioned A type zeolites such as molecular sieve 3A, 4A and 5A, and molecular sieve 13X, Y type zeolites and L type zeolites. Of these, molecular sieve 4A is especially preferable.

After the completion of reaction, an after-treatment and purification by column chromatography are conducted to give the intended α, β-epoxyketone with a high optical purity in a high yield.

In the case where the asymmetric epoxidation of an enone is carried out by using the catalyst solution of the invention, when (R)-binaphthol is used as the component (B), the optical absolute configuration of position 2 (α-position) and position 3 (β-position) of the epoxide produced is (2S, 3R), and, when (S)- binaphthol is used as the component (B), the optical absolute configuration of the same positions is (2R, 3S).

The asymmetric epoxidation of an enone according to the present invention is suitable for the production of intermediates for medicines and pesticides.

The invention will now be specifically described by the following examples that by no means limit the scope of the invention.

In the examples, the optical purity of reaction products was determined by the high performance liquid chromatography using a chiral column OB-H or AD (supplied by Daicel Chem. Ind. Ltd.). The eluting solution was hexane/i-PrOH=2/1–100/1 (vol/vol), and the flow rate was 1 ml/min.

In the case of trans-2,3-epoxy-1,3-diphenylpropan-1-one, chiral column OB-H and an eluting solution of hexane/i-PrOH - 2/1 were used at a flow rate of 1 ml/min. Peaks of enantiomers with optical absolute configurations (2S, 3R) and (2R, 3S) were developed at a retention time of 24 minutes and 32 minutes, respectively.

EXAMPLE 1

A 10 ml eggplant type flask was charged with 506 mg of molecular sieve 4A. The content was heated by a heat gun under reduced pressure (using a vacuum pump) for 30 minutes to be thereby dried. Then the content was cooled to room temperature, and 21.2 mg (0.0758 mmol) of triphenylphosphine oxide, 7.2 mg (0.0251 mmol) of (R)-binaphthol and magnetic stirrer chips were incorporated in the flask. The content was flushed with argon, and then. 1 ml of THF was added and the content was stirred for 5 minutes to dissolve the content. Then 1.52 ml of a solution in THF of 8.0 mg (0.0253 mmol) of lanthanum isopropoxide [La(O-iPr)$_3$] was added and the mixture was stirred for 1 hour to give a catalyst solution.

To the thus-prepared catalyst solution, a solution of 5M (0.15 ml, 0.76 mmol) of TBHP in decane was added, and the mixture was stirred for 30 minutes. Then 1 ml of a THF solution of 105.4 mg (0.506 mmol) of chalcone was added to effect a reaction. It was confirmed by the silica gel thin-layer chromatography that, when 30 minutes elapsed, the reaction was completed.

After the completion of reaction, 500 mg of silica gel and 3 ml of methanol were added and the mixture was stirred for 15 minutes. Then the mixture was filtered and concentrated to yield a residue. The residue was purified by a silica gel column (hexane/AcOEt=30/1) to give trans-(2S,3R)-epoxy-1,3-diphenylpropan-1-one as a colorless transparent oil. Yield: 112.4 mg (99%), optical purity: 96% ee.

EXAMPLE 2

A catalyst solution was prepared by the same procedure and the same reactor as described in Example 1 wherein 24.4 mg (0.0758 mmol) of tri(4-methylphenyl)phosphine oxide was used instead of triphenylphosphine oxide with all other conditions remaining the same. Using the catalyst solution, epoxidation of chalcone was conducted by the same procedure as in Example 1. When the reaction was conducted for 30 minutes, 107.8 mg of trans-(2S,3R)-epoxy-1,3-diphenylpropan-1-one was obtained as a colorless transparent oil. Yield: 95%, optical purity: 94% ee.

EXAMPLE 3

A catalyst solution was prepared by the same procedure and the same reactor as described in Example 1 wherein hexamethyl-phosphortriamide was used instead of triphenylphosphine oxide with all other conditions remaining the same. Using the catalyst solution, epoxidation of chalcone was conducted by the same procedure as in Example 1. When the reaction was conducted for 1.5 hours, 112.4 mg of trans-(2S,3R)-epoxy-1,3-diphenylpropan-1-one was obtained as a colorless transparent oil. Yield: 99%, optical purity: 86% ee.

EXAMPLE 4

A catalyst solution was prepared by the same procedure and the same reactor as described in Example 1 wherein lutidine-N-oxide was used Instead of triphenylphosphine oxide with all other conditions remaining the same. Using the catalyst solution, epoxidation of chalcone was conducted by the same procedure as in Example 1. When the reaction was conducted for 3.0 hours, trans-(2S,3R)-epoxy-1,3-diphenylpropan-l-one was obtained. Yield: 96%, optical purity: 74% ee.

EXAMPLE 5

A catalyst solution was prepared by the same procedure and the same reactor as described in Example 1 wherein 1,3-dimethyl-2-imidazolidinone was used instead of triphenylphosphine oxide with all other conditions remaining the same. Using the catalyst solution, epoxidation of chalcone was conducted by the same procedure as in Example 1. When the reaction was conducted for 3.0 hours, trans-(2S, 3R)-epoxy-1,3-diphenylpropan-l-one was obtained. Yield: 97%, optical purity: 68% ee.

EXAMPLE 6

A catalyst solution was prepared by the same procedure and the same reactor as described In Example 1 wherein tri(2-methylphenyl)phosphine oxide was used instead of triphenylphosphine oxide with all other conditions remaining the same. Using the catalyst solution, epoxidation of chalcone was conducted by the same procedure as in Example 1. When the reaction was conducted for 1.5 hours, trans-(2S,3R)-epoxy-1,3-diphenylpropan-l-one was obtained. Yield: 96%, optical purity: 73% ee.

COMPARATIVE EXAMPLE 1

A catalyst solution was prepared by the same procedure and the same reactor as described in Example 1 wherein triphenylphosphine oxide was not used with all other conditions remaining the same. Using the catalyst solution, epoxidation of chalcone was conducted by the same procedure as in Example 1. When the reaction was conducted for 3.0 hours, trans-(2S,3R)-epoxy-1,3-diphenylpropan-1-one was obtained. Yield: 86%, optical purity: 73% ee.

EXAMPLE 7

A catalyst solution was prepared by the same procedure and the same reactor as described in Example 1. Using the catalyst solution, asymmetric epoxidation was conducted by the same procedure as in Example 1 wherein 87.7 mg of trans-2-methyl-5-phenyl-4-penten-3-one was used as an enone instead of chalcone with all other conditions remaining the same. When the reaction was conducted for 12 hours, 64.2 mg of trans-(4S,5R)-epoxy-2-methyl-5-phenylpentan-3-one was obtained as a colorless transparent oil. Yield: 67%, optical purity: 96% ee.

EXAMPLE 8

A catalyst solution was prepared by the same procedure and the same reactor as described in Example 1. Using the catalyst solution, asymmetric epoxidation was conducted by the same procedure as in Example 1 wherein 87.7 mg of trans-4-methyl-1-phenyl-2-penten-1-one was used as an enone instead of chalcone with all other conditions remaining the same. When the reaction was conducted for 1 hour, 85.2 mg of trans-(2S,3R)-epoxy-4-methyl-1phenylpentan-1-one was obtained as a colorless transparent oil. Yield: 89%, optical purity: 93% ee.

EXAMPLE 9

A catalyst solution was prepared by the same procedure and the same reactor as described in Example 1. Using the catalyst solution, asymmetric epoxidation was conducted by the same procedure as in Example 1 wherein 74.0 mg of trans-4-phenyl-3-buten-2-one was used as an enone instead of chalcone with all other conditions remaining the same. When the reaction was conducted for 6 hours, 75.5 mg of trans-(3S,4R)-epoxy-4-phenylbutan-2-one was obtained as a colorless transparent oil. Yield: 92%, optical purity: 93% ee.

EXAMPLE 10

A catalyst solution was prepared by the same procedure and the same reactor as described in Example 1. Using the catalyst solution, asymmetric epoxidation was conducted by the same procedure as in Example 1 wherein 88.2 mg of trans-6-phenyl-3-hexen-2-one was used as an enone instead of chalcone with all other conditions remaining the same. When the reaction was conducted for 1 hour, 88.6 mg of trans-(3S,4R)-epoxy-6-phenylhexan-1-one was obtained as a colorless transparent oil. Yield: 92%, optical purity: 87% ee.

EXAMPLE 11

A catalyst solution was prepared by the same procedure and the same reactor as described in Example 1. Using the catalyst solution, asymmetric epoxidation of chalcone was conducted by the same procedure as in Example 1 wherein CMHP was used as an oxidizing agent instead of TBHP with all other conditions remaining the same. When the reaction was conducted for 1.0 hour, trans-(2S,3R)-epoxy-1,3-diphenylpropan-1-one was obtained. Yield: 95%, optical purity: 99% ee.

EXAMPLE 12

A catalyst solution was prepared by the same procedure and the same reactor as described in Example 1 wherein the amount of molecular sieve 4A was changed to 100 mg from 506 mg. Using the catalyst solution, asymmetric epoxidation of chalcone was conducted by the same procedure as in Example 1 wherein CMHP was used as an oxidizing agent instead of TBHP with all other conditions remaining the same. When the reaction was conducted for 10 minutes, trans-(2S,3R)-epoxy-1,3-diphenylpropan-1-one was obtained. Yield: 97%, optical purity: 99.8% ee.

EXAMPLE 13

A catalyst solution was prepared by the same procedure and the same reactor as described in Example 1 wherein the amount of molecular sieve 4A was changed to 25 mg from 506 mg. Using the catalyst solution, asymmetric epoxidation of chalcone was conducted by the same procedure as in Example 1 wherein CMHP was used as an oxidizing agent instead of TBHP with all other conditions remaining the same. When the reaction was conducted for 15 minutes, trans-(2S,3R)-epoxy-1,3-diphenylpropan-1-one was obtained. Yield: 91%, optical purity: 99.8% ee.

EXAMPLE 14

A catalyst solution was prepared by the same procedure and the same reactor as described in Example 1. Using the catalyst solution, asymmetric epoxidation of chalcone was conducted by the same procedure as in Example 1 wherein the amount of triphenyl-phosphine oxide was changed to 7.0 mg from 21.2 mg with all other conditions remaining the same. When the reaction was conducted for 1.0 hour, trans-(2S,3R)-epoxy-1,3-diphenylpropan-1-one was obtained. Yield: 91%, optical purity: 93% ee.

What is claimed is:

1. A catalyst composition for organic asymmetric synthesis comprising:
   (A) a lanthanoid element ion;
   (B) a binaphthol represented by the following general formula

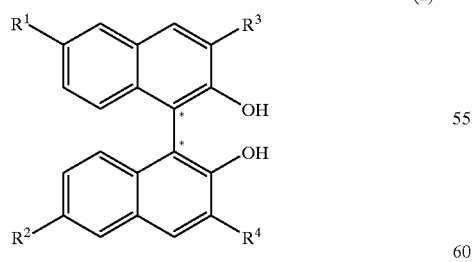

(1)

wherein $R^1$, $R^2$, $R^3$ and $R^4$ independently represent a hydrogen atom, a straight chain, branched chain or cyclic alkyl group having 1 to 10 carbon atoms, a straight chain, branched chain or cyclic alkoxy group having 1 to 10 carbon atoms, a straight chain, branched chain or cyclic alkyloxyalkyl group having 2 to 10 carbon atoms, a straight chain, branched chain or cyclic alkyloxyalkoxy group having 2 to 10 carbon atoms, a straight chain, branched chain or cyclic alkylamino group having 1 to 10 carbon atoms, an aromatic group having 5 to 14 carbon atoms, an aromatic group having 5 to 14 carbon atoms and having a substituent which is an alkyl group having 1 to 5 carbon atoms, or a halogen atom; and * signifies that the carbon atom adjacent thereto is optically active; and (C) at least one compound selected from the group consisting of:
   (i) compounds represented by the following general formula (2):

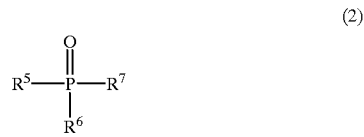

(2)

wherein $R^5$, $R^6$ and $R^7$ independently represent a straight chain, branched chain or cyclic alkyl group having 1 to 10 carbon atoms, an aromatic group having 5 to 14 carbon atoms, an aromatic group having 5 to 14 carbon atoms and having a substituent which is an alkyl group with 1 to 5 carbon atoms, or a group represented by the following formula:

wherein $R^8$ and $R^9$ independently represent a straight chain, branched chain or cyclic alkyl group having 1 to 10 carbon atoms, an aromatic group having 5 to 14 carbon atoms, a straight chain, branched chain or cyclic alkyl group having 1 to 5 carbon atoms and having a substituent which is an aromatic group with 5 to 14 carbon atoms, or an aromatic group having a substituent which is an aromatic group with 5 to 14 carbon atoms, and $R^8$ and $R^9$ may be combined together to form an alkylene group having 2 to 6 carbon atoms; and (ii) compounds represented by the following general formula (3):

(3)

wherein A represents a carbon or nitrogen atom; and, when A is a carbon atom, $R^{10}$ and $R^{11}$ independently represent an amino group having two substituents each of which is a straight chain, branched chain or cyclic alkyl group having 1 to 10 carbon atoms, wherein $R^{10}$ and $R^{11}$ may be combined together with A to form a nitrogen-containing ring, or $R^{10}$ and $R^{11}$ independently represent an amino group having two substituents each of which is an aromatic group having 5 to 14 carbon atoms, and the bond between A and O is a double bond; and, when A is a nitrogen atom, $R^{10}$ and $R^{11}$ are combined together with A to form a nitrogen-containing aromatic ring, and the bond between A and O is a single bond.

2. The catalyst composition for organic asymmetric synthesis according to claim 1, which comprises (A) 1 mole of the lanthanoid element ion; (B) 1 to 3 moles of the binaphthol of the general formula (1); and (C) 1 to 10 moles of at least one compound selected from the group consisting of (i) the compounds of the general formula (2) and (ii) the compounds of the general formula (3).

3. The catalyst composition for organic asymmetric synthesis according to claim 1, wherein the lanthanoid element ion (A) is an ion of a lanthanoid element selected from the group consisting of scandium, yttrium, lanthanum, cerium, praseodymium, neodymium, samarium, europium, gadolinium, terbium, dysprosium, holmium, erbium, thulium, ytterbium and lutecium.

4. The catalyst composition for organic asymmetric synthesis according to claim 1, wherein the binaphthol (B) of the formula (1) is a compound selected from the group consisting of (R)-binaphthol, (R)-3,3'-dimethoxybinaphthol, (R)-3,3'-methoxyethoxybinaphthol, (R)-6,6'-diphenylbinaphthol, (R)-6,6'-dibromobinaphthol, (R)-6,6'-dinaphthylbinaphthol, (R)-6,6'-dimethoxybinaphthol, (S)-binaphthol, (S)-3,3'-dimethoxybinaphthol, (S)-3,3'-methoxyethoxybinaphthol, (S)-6,6'-diphenylbinaphthol, (S)-6,6'-dibromobinaphthol, (S)-6,6'-dinaphthylbinaphthol and (S)-6,6'-dimethoxybinaphthol.

5. The catalyst composition for organic asymmetric synthesis according to claim 1, wherein the compound of the general formula (2) is selected from the group consisting of triphenylphosphine oxide, tri(p-methylphenyl),phosphine oxide, hexamethylphosphoric triamide and tripiperidinophosphine oxide.

6. A catalyst solution for organic asymmetric synthesis, which comprises a catalyst composition as claimed in claim 1 and an ether solvent.

7. The catalyst solution for organic asymmetric synthesis according to claim 6, which further compries a zeolite.

8. A catalyst composition for asymmetric epoxation of an enone comprising:

(A) lanthanum triisopropoxide, (B) binaphthol, and (C) at least one compound selected from the group consisting of lutidine-N-oxide, 1,3-dimethyl-2-imidazolidinone, hexamethyl-phosphoric triamide, triphenylphosphine oxide, tri(2-methylphenyl) phosphine oxide and tri(4-methylphenyl)phosphine oxide.

* * * * *

UNITED STATES PATENT AND TRADEMARK OFFICE
CERTIFICATE OF CORRECTION

PATENT NO. : 6,201,123 B1
DATED : March 13, 2001
INVENTOR(S) : Daikai et al.

It is certified that error appears in the above-identified patent and that said Letters Patent is hereby corrected as shown below:

<u>Title page,</u>
Item (73) Assignee delete "Techno Polymer Co., Ltd. Tokyo, (JP)" and insert
-- Tosoh Corporation, Yamaguchi, (JP) --.

Signed and Sealed this

Twenty-eighth Day of August, 2001

*Attest:*

*Attesting Officer*

NICHOLAS P. GODICI
*Acting Director of the United States Patent and Trademark Office*